(12) United States Patent
Avinun-Kalish et al.

(10) Patent No.: US 7,659,506 B2
(45) Date of Patent: Feb. 9, 2010

(54) METHOD AND SYSTEM FOR GENERATING AND REVIEWING A THIN SAMPLE

(75) Inventors: Michal Avinun-Kalish, Nes Ziona (IL); Jacob Levin, Rehovot (IL); Dror Shemesh, Hod Hasharon (IL)

(73) Assignee: Applied Materials, Israel, Ltd., Rehovot (IL)

( * ) Notice: Subject to any disclaimer, the term of this patent is extended or adjusted under 35 U.S.C. 154(b) by 260 days.

(21) Appl. No.: 11/861,206

(22) Filed: Sep. 25, 2007

(65) Prior Publication Data

US 2009/0078867 A1   Mar. 26, 2009

(51) Int. Cl.
*G01N 23/22* (2006.01)

(52) U.S. Cl. .............. 250/304; 250/306; 250/307; 250/309; 250/310; 250/311

(58) Field of Classification Search ............ 250/304, 250/306, 307, 309, 310, 311
See application file for complete search history.

(56) References Cited

U.S. PATENT DOCUMENTS

| 6,670,610 | B2 | 12/2003 | Shemesh et al. |
| 7,005,636 | B2 | 2/2006 | Tappel |
| 2004/0016880 | A1 | 1/2004 | Reiner et al. |
| 2006/0011867 | A1 | 1/2006 | Kidron et al. |

*Primary Examiner*—Jack I Berman
*Assistant Examiner*—Hanway Chang
(74) *Attorney, Agent, or Firm*—Sonnenschein Nath & Rosenthal LLP

(57) ABSTRACT

A system and method for generating a thin sample, the method includes: milling an intermediate section of a thin sample such as to enable an upper portion of the thin sample to tilt in relation to a lower portion of the thin sample; wherein the lower portion is connected to a wafer from which the thin sample was formed. A system and method for inspecting a thin sample, the method includes: A method for inspecting a thin sample, the method comprising: illuminating, by a charged particle beam, a tilted upper portion of a thin sample that is connected, via a milled intermediate section, to a lower portion of the thin sample; wherein the lower portion is connected to a wafer from which the thin sample was formed; and collecting particles and photons resulting from the illumination.

31 Claims, 9 Drawing Sheets

Illuminating, by a charged particle beam, a tilted upper portion of a thin sample that is connected, via a milled intermediate section, to a lower portion of the thin sample; wherein the lower portion is connected to a wafer from which the thin sample was formed. 310

Collecting particles resulting from the illumination. 320

METHOD AND SYSTEM FOR GENERATING AND REVIEWING A THIN SAMPLE

FIELD OF THE INVENTION

The invention relates to methods and systems for generating a thin sample and for reviewing a thin sample and especially a thin sample of microscopic dimensions.

BACKGROUND OF THE INVENTION

In the study of electronic materials and processes for fabricating such materials into an electronic structure, a specimen of the electronic structure is frequently used for microscopic examination for purposes of failure analysis and device validation. For instance, a specimen of an electronic structure such as a silicon wafer is frequently analyzed in scanning electron microscope (SEM) and transmission electron microscope (TEM) to study a specific characteristic feature in the wafer. Such characteristic feature may include the circuit fabricated and any defects formed during the fabrication process. An electron microscope is one of the most useful equipment for analyzing the microscopic structure of semiconductor devices.

In preparing specimens of an electronic structure for electron microscopic examination, various polishing and milling processes can be used to section the structure until a specific characteristic feature is exposed.

As device dimensions are continuously reduced to the sub-half-micron level, the techniques for preparing specimens for study in an electron microscope have become more important.

SEM has a large interaction volume and collects mixed information from the surface of the inspected wafer and from deeper portions of the inspected wafer. TEM, and especially cross sectioning based TEM, enables to acquire high resolution information from sub-surface regions of the wafer. TEM requires to generate an electron transparent thin sample, and then extract the thin sample. The extraction of the sample is time consuming and can damage the thin sample.

There is an ongoing need for methods and systems for generating thin samples from wafers for improved analysis of a wafer and especially to provide a reliable and fast automatic process for generating this samples and analyzing them.

SUMMARY OF THE INVENTION

A system for generating a thin sample, the system includes: a miller, adapted to mill an intermediate section of a thin sample such as to enable an upper portion of the thin sample to tilt in relation to a lower portion of the thin sample; wherein the lower portion is connected to a wafer from which the thin sample was formed; and an inspection aiding material placement unit, adapted to place an inspection aiding material at a location that is selected such that when the thin sample is illuminated by a charged particle beam multiple charged particles that pass through the tilted upper portion of the thin sample will interact with the inspection aiding material.

A system for inspecting a thin sample, the system includes: a miller, adapted to mill an intermediate section of a thin sample such as to enable an upper portion of the thin sample to tilt in relation to a lower portion of the thin sample; wherein the lower portion is connected to a wafer from which the thin sample was formed; and an inspection unit, adapted to direct a charged particle beam towards the upper portion and to collect particles resulting from the illumination.

A method for generating a thin sample, the method includes: milling an intermediate section of a thin sample such as to enable an upper portion of the thin sample to tilt in relation to a lower portion of the thin sample; wherein the lower portion is connected to a wafer from which the thin sample was formed.

A method for inspecting a thin sample, the method includes: illuminating a tilted upper portion of a thin sample that is connected, via a milled intermediate section, to a lower portion of the thin sample; wherein the lower portion is connected to a wafer from which the thin sample was formed; and collecting particles resulting from the illumination.

BRIEF DESCRIPTION OF THE DRAWINGS

FIG. 6 is a flow chart of a method for inspecting a thin sample according to an embodiment of the invention.

DETAILED DESCRIPTION OF THE DRAWINGS

Figure 1A:
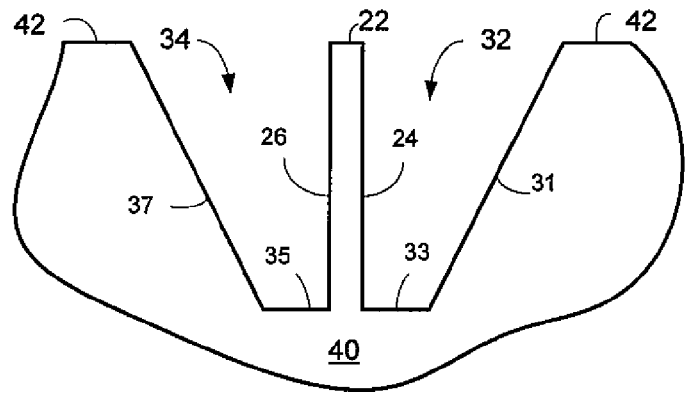
FIGS. 1A-1D are cross sectional views of a thin sample and its surroundings during preparation of the thin sample, according to various embodiments of the invention.

It should be understood that the class of embodiments described herein provides only a few examples of the many advantageous uses of the innovative teachings herein. In general, statements made in the specification of the present application do not necessarily delimit any of the various claimed inventions. Moreover, some statements may apply to some inventive features but not to others. In addition all figures are out of scale. Thus, for example the dimensions of the thin sample are much smaller that the dimensions of the trenches that surrounds it, the distance between the thin sample and the detectors is much longer than the dimensions of the thin sample and the size of the various detectors are much larger than the dimensions of the thin sample.

In accordance with many embodiments of the present invention, a disclosed method for thin sample formation begins with milling the surrounding of a thin sample such that the thin sample is connected to the object from which it is formed at its lower part only. An intermediate section of the thin sample is milled such as to enable the upper portion of the thin sample to tilt. The tilted upper portion can then be inspected by directing a charge particle beam towards the thin sample. Conveniently, the charged particle beam is almost perpendicular to the tilted upper portion but this is not necessarily so.

The thin sample (also referred to as lamella) exposes sub-layer portions of the wafer. By illuminating the tilted upper portion of the thin sample and collecting charged particles scattered or reflected from the thin sample information about the sub-layer portions of the wafer can be acquired. The thin sample can be at least partially transparent to electrons but this is not necessarily so.

Yet according to an embodiment of the invention TEM-like information is acquired. This acquisition involves allowing charged particles to pass through the thin sample (especially its tilted upper portion), to interact with an inspection aiding material and detecting particles that are generated due to an interaction between the inspection aiding material and these charged particles. The inspection aiding material is placed in a location that is selected such that charged particles that pass through the thin sample can interact with the inspection aiding material.

It is noted that disconnecting the lower part of a thin sample from the object (from which the thin sample is formed) is complex and time consuming. The extraction of the thin sample and placement on a dedicated SEM or TEM sample holder is even more time consuming and complex. By generating and inspecting a thin sample without disconnecting its lower portion from the object the whole generation and inspection process is much faster and can be characterized by much higher success rate.

FIGS. 1A-1C, 2A-2B, 3A-3B illustrate various stages in the generation of a thin sample that includes a tilted upper portion. FIGS. 1D, 2C and 3C illustrate the placement of inspection aiding material. FIG. 4A illustrates an inspection of particles that are either scattered or reflected from the thin sample while FIG. 4B illustrates an inspection of a thin sample that utilizes the inspection aiding material. FIG. 4C illustrates a detection of photons emitted from an inspection aiding material as well as a detection of charged particles scattered or reflected from the thin sample.

Thin sample 20 is typically generated by forming trenches from both sides of the thin sample and then separating the other two sides of the thin sample by performing a relatively small cut. Typically, the trenches are formed using a Focused Ion Beam. Trench and cut forming techniques are known in the art. Examples of methods for forming such trenches and cuts are illustrated in U.S patent application 2006/0011867 that is incorporated herein by reference.

It is further noted that after the trenches are formed the thin sample can be thinned to a desired thickness.

FIG. 1A illustrates first and second trenches 32 and 34. First trench 32 has an inclined face 31, bottom surface 33 and a vertical face 24 that is a sidewall of thin sample 20. Second trench 34 has an inclined face 37, bottom surface 35 and a vertical face 26 that is a sidewall of thin sample 20. It is noted that the shape of the trenches can differ from the shape illustrated in the various figures and that typically the surfaces of each trench are relatively textured. Thin sample 20 has an upper surface 22 that is conveniently a part of the upper surface of the wafer from which the thin sample was made.

Conveniently, upper part 22 is covered by deposition prior to the formation of trenches.

The trenches can be formed and the thin sample can be thinned or eroded by using a miller that can be oriented in relation to the object, but this is not necessarily so. This orientation can be achieved by tilting the object, tilting the miller or by using electrical or magnetic tilt of the beam of the miller or a combination thereof. A method for directing a miller is described in U.S. Pat. No. 6,670,610 of Shemesh et al. which is incorporated herein by reference. A method for generating a lamella is described in U.S. patent application 2006/0011867 which is incorporated herein by reference. Various method and systems for generating and extracting a lamella are also illustrated in U.S. Pat. No. 7,005,636 of Tappel, and U.S, patent application serial number 2004/0016880.

The thickness of the thin sample is defined as the distance between vertical faces 24 and 26. The width of the trench is the distance between inclined faces 31 and 37. Typically, the thickness of thin sample 20 is much smaller than the width of each trench. The thickness of the thin sample can be less than a micron. The width of the trench is in the order of twice the distance between face 22 and either one of inclined faces 33 or 35.

Figure 2A:
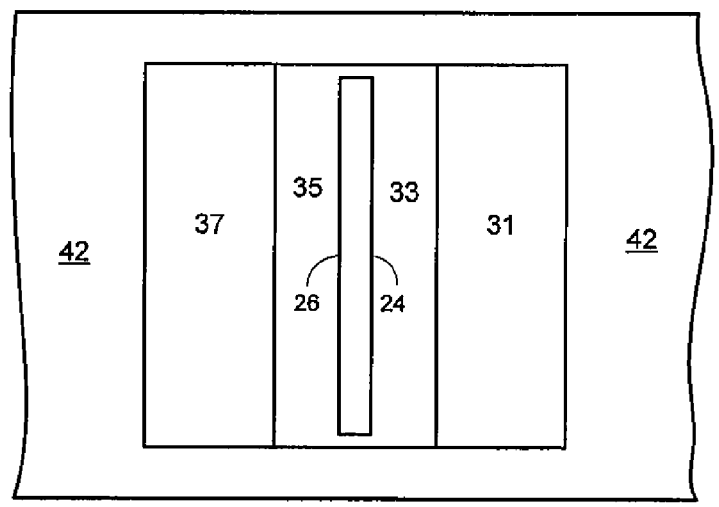
FIGS. 2A-2C are top views of a thin sample and its surroundings during a preparation of the thin sample, according to various embodiments of the invention.

Referring back to the mentioned above figures, the preparation of the thin sample starts (as illustrated by FIGS. 1A and 2A) by milling an object such as to form a thin sample (that can have a rectangular shape) that is connected to the object only at its lower portion.

According to an embodiment of the invention once the thin sample is formed inspection aiding material can be deposited. According to another embodiment of the invention the inspection aiding material is deposited before the sample is thinned or bent.

Figure 1B:
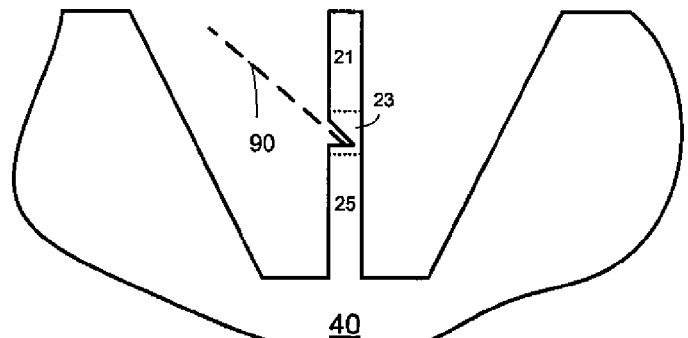
Figure 3A:
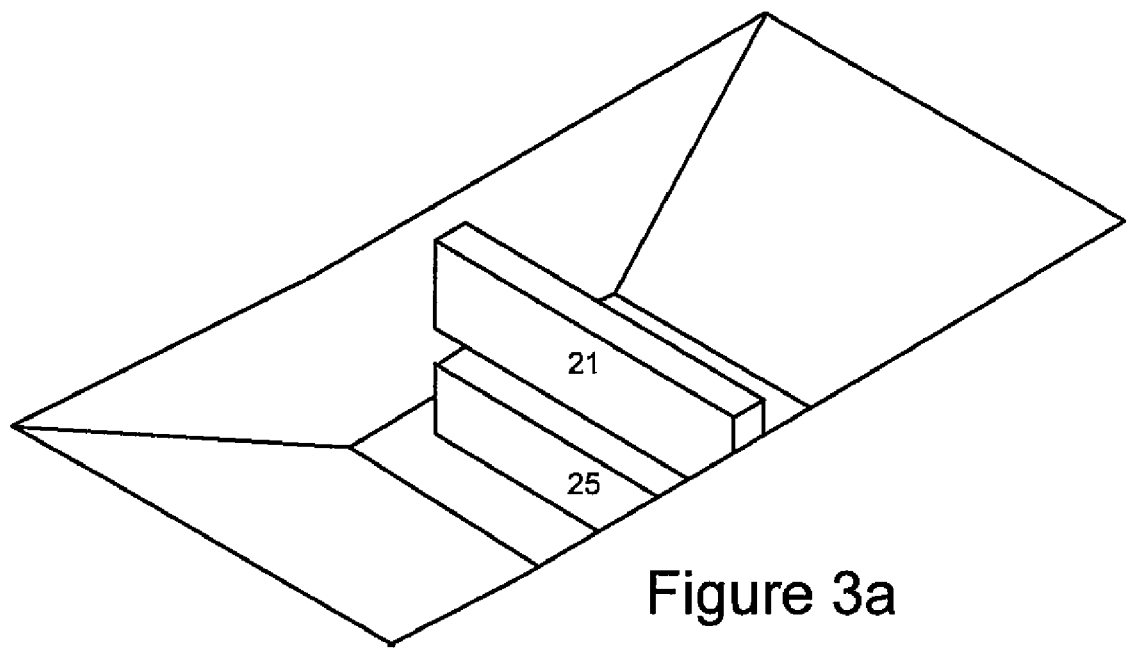
FIGS. 3A-3C are perspective views of a thin sample and its surroundings during a preparation of the thin sample, according to various embodiments of the invention.
Figure 4A:
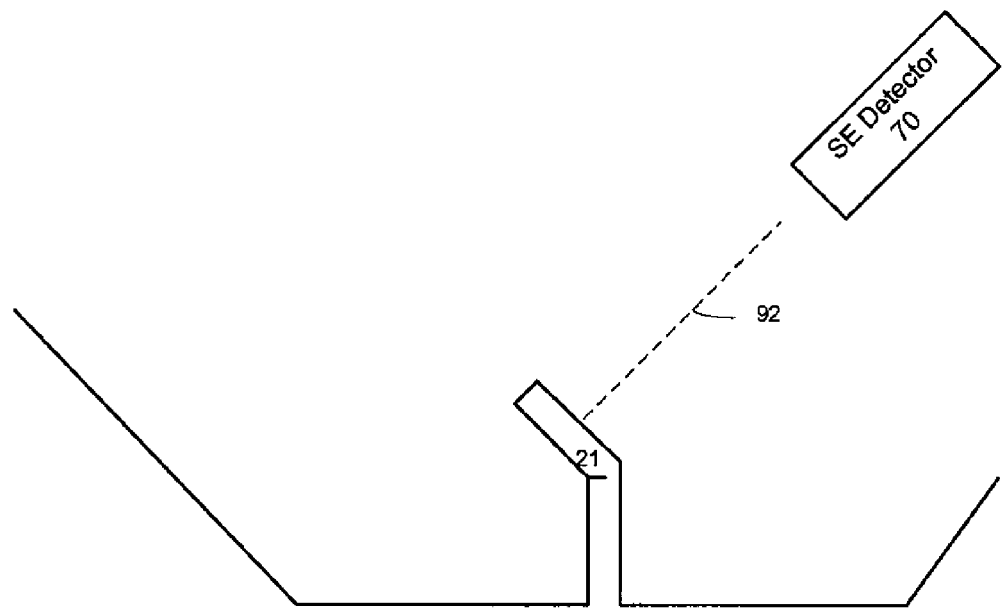
FIGS. 4A-4C illustrate an inspection of the thin sample according to various embodiments of the invention.
Figure 4B:
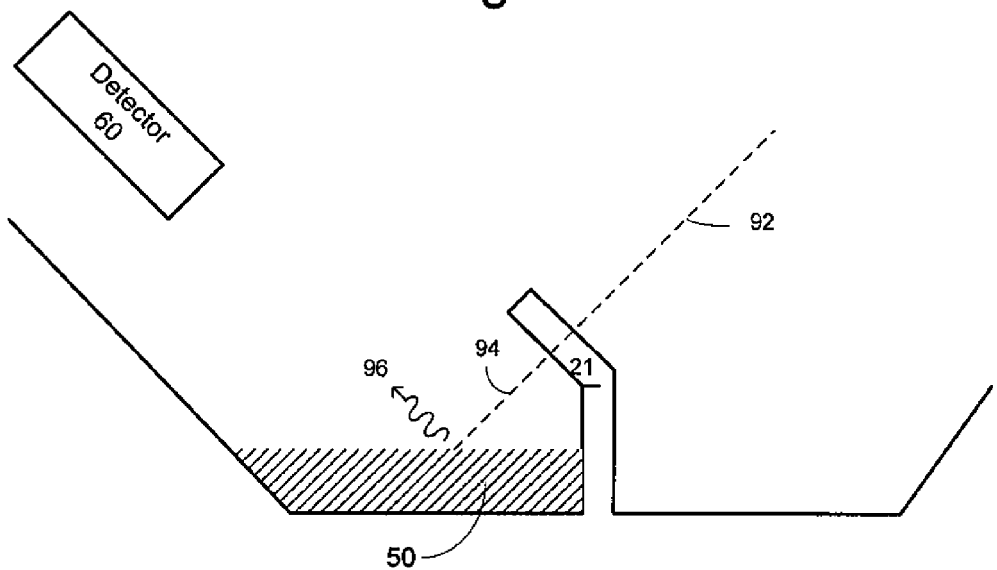
Figure 4C:
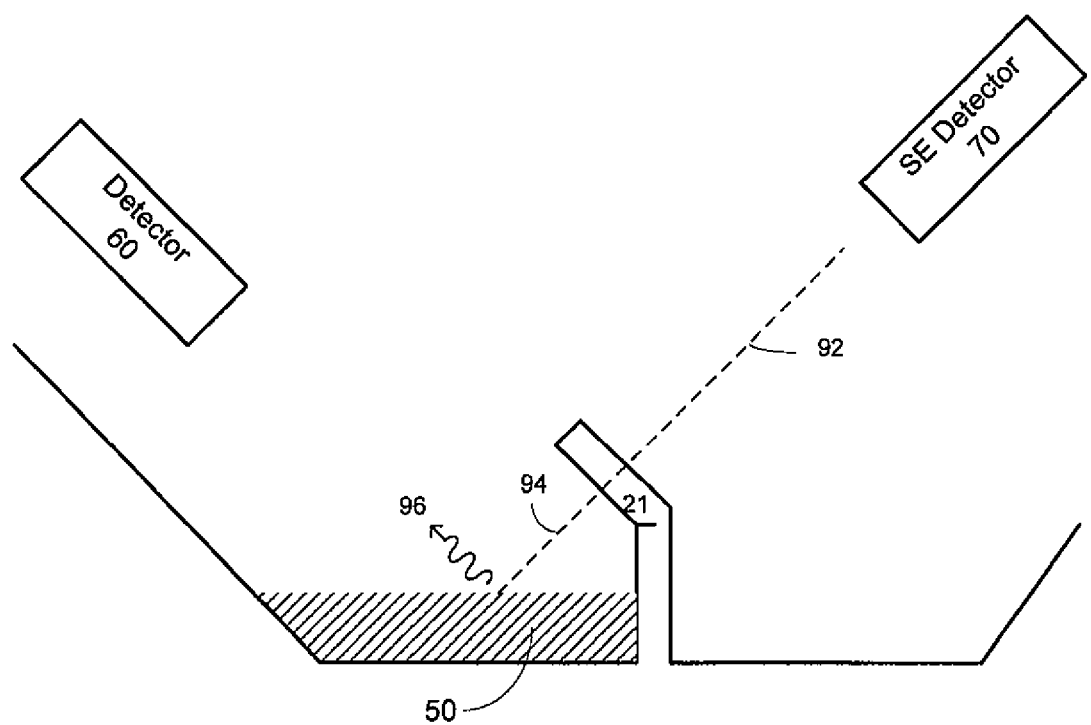

If the deposition is not performed then the process proceeds (as illustrated by FIGS. 1B and 3A) by milling intermediate section 23 of thin sample 22. Intermediate section 23 is located between upper portion 21 and lower portion 25 of thin sample 20. The milling (or eroding) does not disconnect upper portion 21 from lower portion 25 but rather introduces a longitudinal cavity that thins the intermediate section. The cavity can have a "V" shaped cross section but this is not necessarily so. Conveniently, there should be an angle between the upper and lower surfaces of the cavity and this angle determines the bending angle of the upper portion 21 of the thin sample. The milling is executed in a manner that enables upper portion 21 to be tilted towards a certain direction, such as to substantially close the cavity that was formed within intermediate section 23. The tilt can result from electrostatic attraction between the upper and lower portion but this is not necessarily so. It is further noted that upper portion 21 can be bombarded by a focused ion beam in order to expedite its tilt.

Figure 1C:
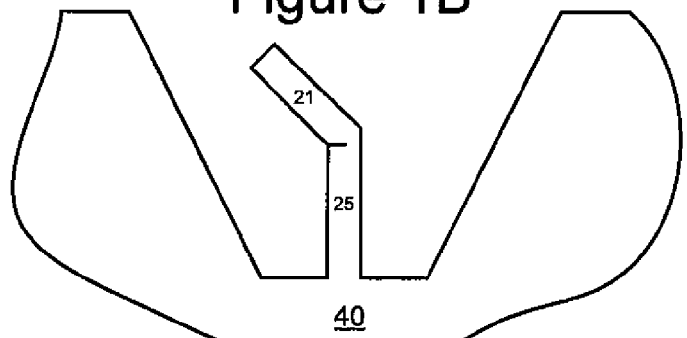
Figure 1D:
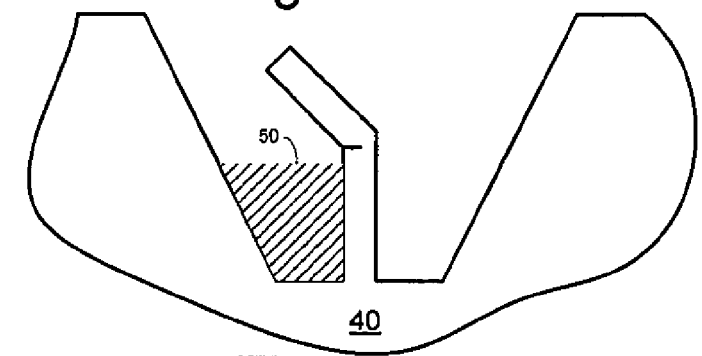
Figure 2B:
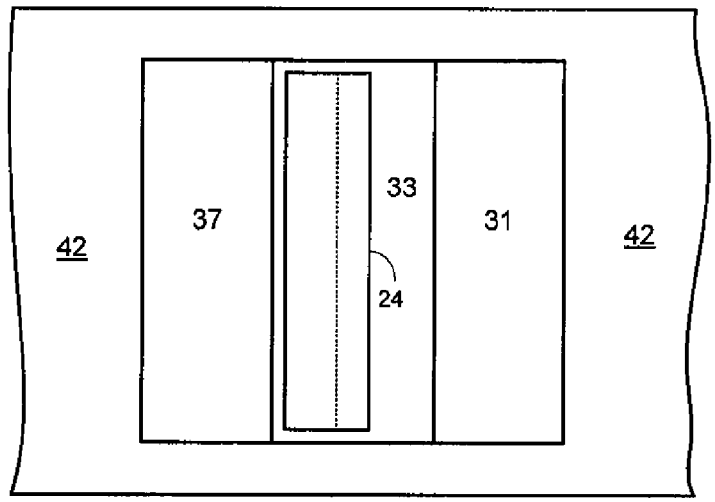
Figure 2C:
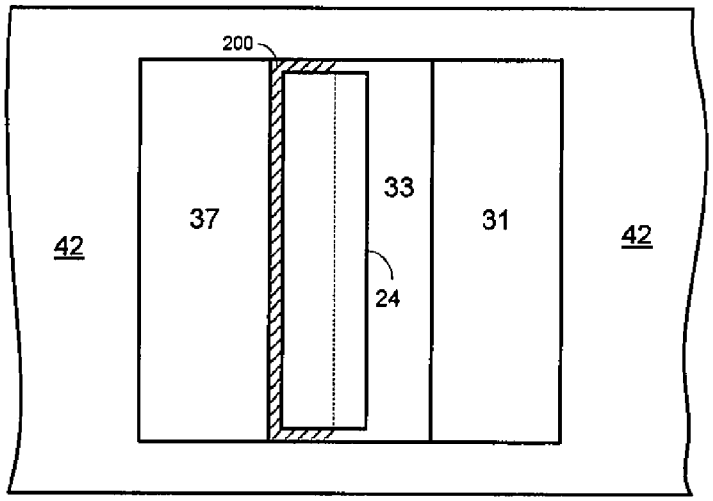
Figure 3B:
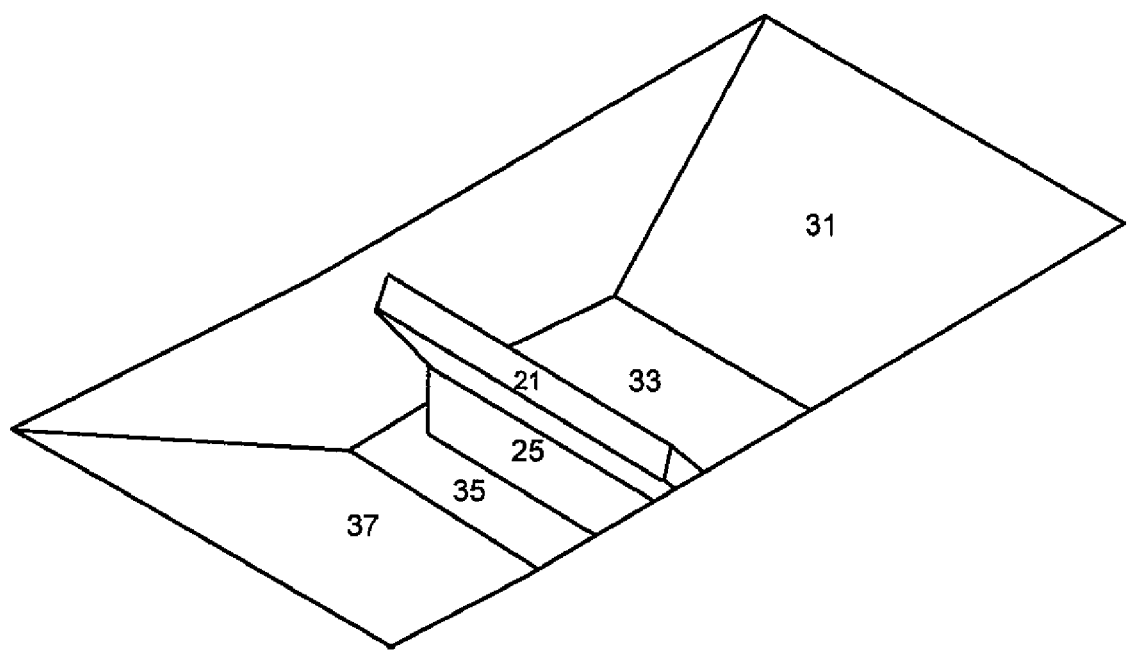
Figure 3C:
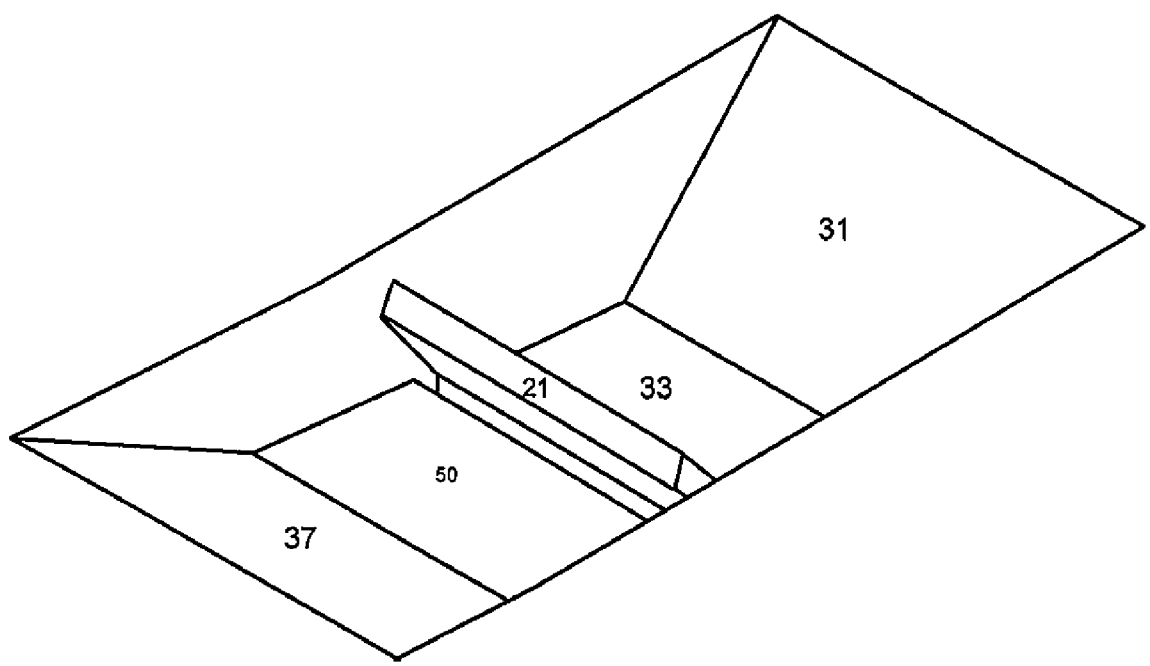

FIGS. 1C, 2B and 3B illustrate thin sample 20 and its close surroundings after upper portion 21 is tilted to provide a tilted upper portion. It is noted that the location of intermediate section 23 can be determined in response to the sub-surface area that should be inspected as well as to the ability to illuminate upper portion 21 (affected from the geometry of the trench, location of illumination optics, detectors and the like). Although the mentioned above figures illustrate an intermediate section that is located at the center of thin sample 20, this is not necessarily so.

This thin sample (including a tilted upper portion) can be inspected by directing a charged particle beam towards at least the tilted upper portion 21. Charged particle beams that are scattered from the thin sample (or at least from its upper portion) can be collected by utilizing conventional SEM techniques. FIG. 4A illustrates an illumination of a thin sample 20 and the detection of reflected secondary electrons by a detector such as a backscattered electron detector or a secondary electron (SE) detector 70. It is noted that other detectors can be used. In addition, the detection can be executed by multiple detectors.

Yet according to an embodiment of the invention the generation process of the thin sample can also include providing an inspection aiding material in proximity to the thin sample. The location of the inspection aiding material is selected such during an inspection of the thin sample, charged particles that pass through the thin sample (and especially though upper portion 21) and interact with the inspection aiding material such as to produce charged particles and/or photons that are then detected by one or more detectors.

The inspection aiding material can be selected in accordance to the particles that should be detected. A charged particle to photon conversion requires a scintillating material. On the other hand, detection of x-ray particles and/or backscattered electrons requires a metallic material or other materials with high atomic number.

It is noted that the placement of the inspection aiding material can be performed before milling the intermediate section of the thin sample. The placement can involve using various deposition techniques. Conveniently, the placement can be followed by cleaning or thinning the thin sample.

FIGS. 1D and 3C illustrate inspection aiding material 50 that is placed within second trench 34. It is noted that a portion of the inspection aiding material can be expected to be deposited within second trench 32, but this is not necessarily so. For convenience of explanation this was not illustrated in the figure.

FIG. 4B illustrates an inspection process during which thin sample 20 is illuminated by a charged particle beam 92, multiple charge particles 94 pass through the upper portion 21, interact with the inspection aiding material 50 and form particles (illustrated as photons 96) that are detected by detector 60.

FIG. 4C illustrates an inspection process during which thin sample 20 is illuminated by a charged particle beam 92, multiple charge particles 94 pass through the upper portion 21, interact with the inspection aiding material 50 and form particles (illustrated as photons 96) that are detected by detector 60. In addition, particles that are scattered and/or reflected from upper portion 21 are detected by secondary electron detector 70.

Figure 5:
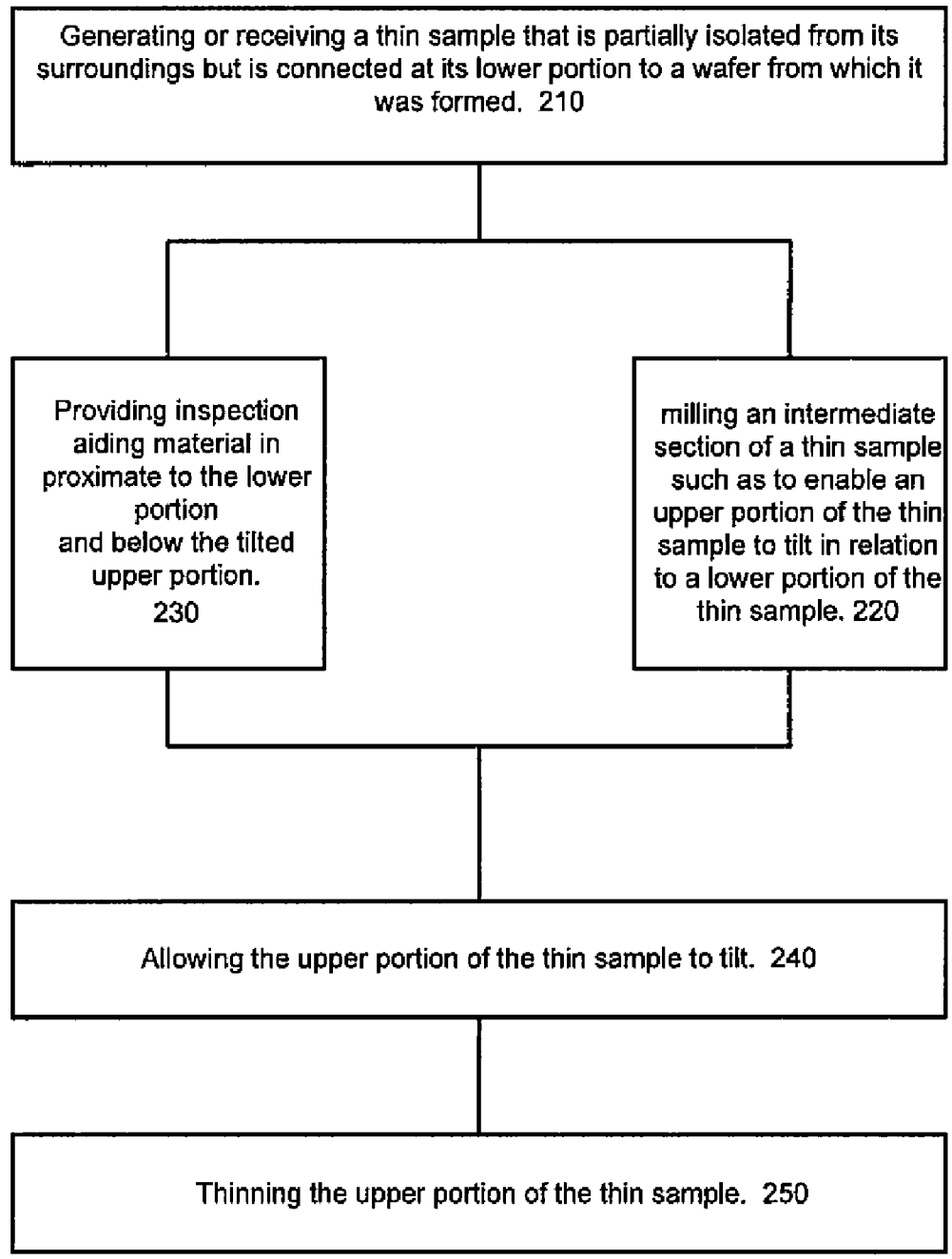
FIG. 5 is a flow chart of a method for generating a thin sample according to an embodiment of the invention.

FIG. 5 illustrates method 200 for generating a thin sample, according to an embodiment of the invention.

Method 200 starts by stage 210 or generating or receiving a thin sample that is partially isolated from its surroundings but is connected at its lower portion to a wafer from which it was formed.

According to an embodiment of the invention (and especially if stage 230 is executed) the thin sample is transparent to charged particles, but this is not necessarily so. If stage 230 is not executed than the thin sample can be thicker and not transparent to electrons.

Stage 210 can be followed by stage 220 and additionally or alternatively, by stage 230.

Stage 220 includes milling an intermediate section of a thin sample such as to enable an upper portion of the thin sample to tilt in relation to a lower portion of the thin sample. Conveniently, at this stage the thin sample can not be inspected by a TEM. It is noted that one or more cavities can be formed (within thin sample) in order to enable the upper portion to tilt.

Stage 230 includes depositing an inspection aiding material in proximate to the lower portion and below the tilted upper portion. The location of the inspection aiding material is selected such to assist in an inspection of the thin sample using transmissive inspection. During the transmissive inspection the thin sample is illuminated by a charged particle beam. Multiple charged particles pass through the tilted upper portion of the thin sample and interact with the inspection aiding material.

According to an embodiment of the invention the placed inspection aiding material is adapted to emit backscattered electrons in response to an interaction with the multiple charged particles.

According to an embodiment of the invention the placed inspection aiding material is adapted to emit photons in response to an interaction with the multiple charged particles.

According to an embodiment of the invention the placed inspection aiding material is adapted to emit x-ray photons in response to an interaction with the multiple charged particles.

Stages 220 and 230 are followed by stage 240 of allowing the upper portion of the thin sample to tilt.

Conveniently, the thin sample is milled in order to enable the upper portion to be tilted at an acute angle in relation to an upper surface of the thin sample, and alternatively or additionally to be tilted at an acute angle in relation to the lower portion of the thin sample. The acute angle can be about forty five degrees, but other angles can be selected.

Stage 240 can be followed by stage 250 of thinning the upper portion of the thin sample.

FIG. 6 illustrates method 300 for inspecting a thin sample, according to an embodiment of the invention.

Method 300 starts by stage 310 of illuminating, by a charged particle beam, a tilted upper portion of a thin sample that is connected, via a milled intermediate section, to a lower portion of the thin sample; wherein the lower portion is connected to a wafer from which the thin sample was formed.

Stage 310 is followed by stage 320 of collecting particles resulting from the illumination.

Stage 320 can include at least one of the following or a combination thereof: (i) collecting charged particles reflected or scattered from the thin sample; (ii) collecting charged particles and/or photons resulting from an interaction between an inspection aiding material and charged particles that pass through the upper portion of the thin sample.

It is noted that stage 320 can include collecting particles such as but not limited to photons, x-ray photons and backscattered electrons.

Figure 7:
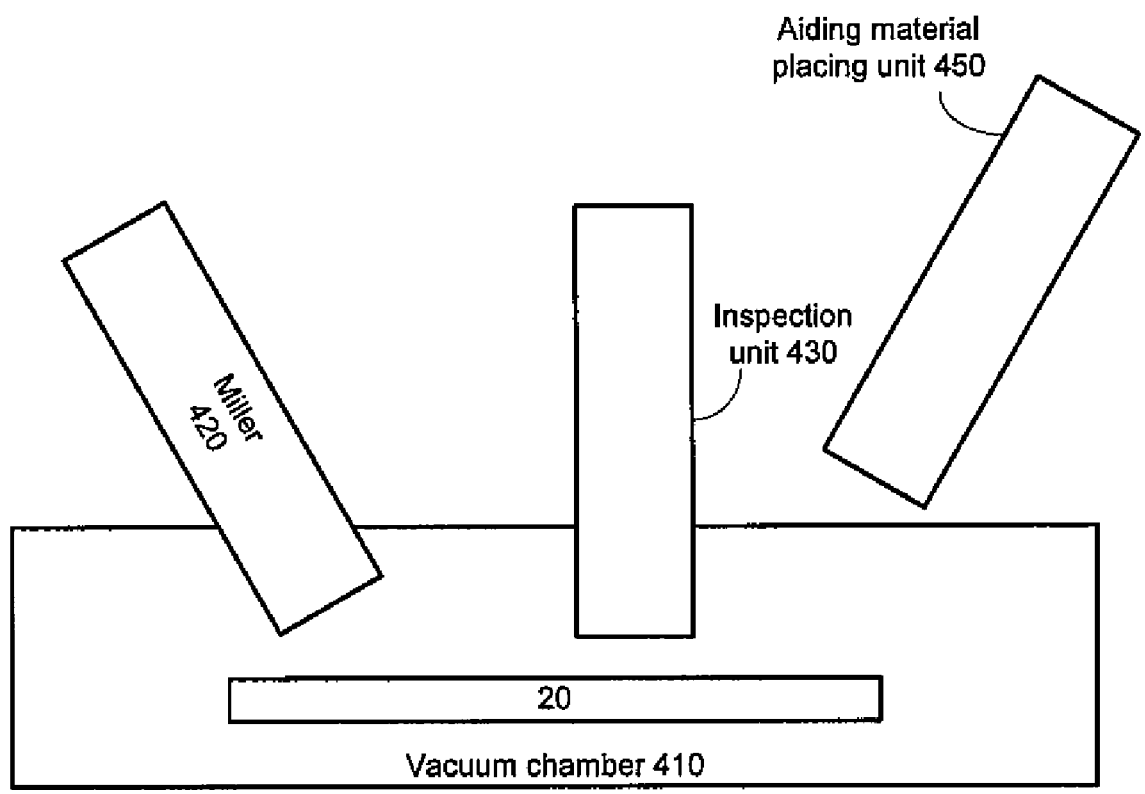
FIG. 7 illustrates a system according to an embodiment of the invention.

FIG. 7 illustrates system 400 according to an embodiment of the invention.

System 400 includes vacuum chamber 410, miller 420 and inspection unit 430. An object, such as wafer 20 is positioned within vacuum chamber 410 while miller 420 and inspection unit 430 are partially situated within vacuum chamber 410. It is noted that during the inspection process inspection unit 430 (or at least one detector of inspection unit 430) are tilted in relation to wafer 20.

Miller 420 is adapted to mill an intermediate section of a thin sample such as to enable an upper portion of the thin sample to tilt in relation to a lower portion of the thin sample; wherein the lower portion is connected to a wafer from which the thin sample was formed. Inspection unit 430 is adapted to direct a charged particle beam towards the upper portion and to collect particles resulting from the illumination.

Conveniently system 400 also includes inspection aiding material placement unit 450 that is adapted to place an inspection aiding material at a location that is selected such that when the thin sample is illuminated by a charged particle beam multiple charged particles that pass through the tilted upper portion of the thin sample will interact with the inspection aiding material.

Conveniently, miller 420 uses a focus ion beam for the milling and inspection unit 430 directs a charged electron beam towards the thin sample. Inspection unit 430 can include one or more detectors that can detect secondary electrons and/or backscattered electrons and/or photons. System 400 can include a FIB column and a SEM column, as illustrated in U.S. Pat. No. 6,670,610 of Shemesh et al.

It is noted that the milling of the thin sample can enable the thin sample to bend, and that such bending is equivalent to the tilt of the upper portion.

The present invention can be practiced by employing conventional tools, methodology and components. Accordingly, the details of such tools, component and methodology are not set forth herein in detail. In the previous descriptions, numerous specific details are set forth, in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method for generating a thin sample, the method comprising:
    milling an intermediate section of a thin sample such as to enable an upper portion of the thin sample to tilt in relation to a lower portion of the thin sample; wherein the lower portion is connected to a wafer from which the thin sample was formed.

2. The method according to claim 1 comprising milling the intermediate section such as to enable the upper portion to be tilted at substantially forty five degrees in relation to the lower portion.

3. The method according to claim 1 comprising milling the intermediate section such as to enable the upper portion to be tilted at substantially forty five degrees in relation to an upper surface of the object.

4. The method according to claim 1 comprising milling the intermediate section such as to enable the upper portion to be tilted at an acute angle in relation to an upper surface of the object.

5. The method according to claim 1 further comprising thinning the upper portion.

6. The method according to claim 1 further comprising placing an inspection aiding material in proximate to the lower portion and below the tilted upper portion.

7. The method according to claim 1 further comprising placing an inspection aiding material at a location that is selected such that when the thin sample is illuminated by a charged particle beam multiple charged particles that pass through the tilted upper portion of the thin sample will interact with the inspection aiding material.

8. The method according to claim 7 comprising placing an inspection aiding material that is adapted to emit backscattered electrons in response to an interaction with the multiple charged particles.

9. The method according to claim 7 comprising placing an inspection aiding material that is adapted to emit photons in response to an interaction with the multiple charged particles.

10. The method according to claim 7 comprising placing an inspection aiding material that is adapted to emit x-ray photons in response to an interaction with the multiple charged particles.

11. A method for inspecting a thin sample, the method comprising: illuminating, by a charged particle beam, a tilted upper portion of a thin sample that is connected, via a milled intermediate section, to a lower portion of the thin sample; wherein the lower portion is connected to a wafer from which the thin sample was formed; and collecting particles resulting from the illumination.

12. The method according to claim 11 wherein the collecting comprises collecting charged particles reflected or scattered from the thin sample.

13. The method according to claim 11 wherein the collecting comprises collecting particles resulting from an interaction between an inspection aiding material and charged particles that pass through the upper portion of the thin sample.

14. The method according to claim 11 wherein the collecting comprises collecting backscattered electrons resulting from an interaction between an inspection aiding material and charged particles that pass through the upper portion of the thin sample.

15. The method according to claim 11 wherein the collecting comprises collecting x-ray photons resulting from an interaction between an inspection aiding material and charged particles that pass through the upper portion of the thin sample.

16. The method according to claim 11 wherein the collecting comprises collecting photons resulting from an interaction between an inspection aiding material and charged particles that pass through the upper portion of the thin sample.

17. A system for inspecting a thin sample, the system comprises:
    a miller, adapted to mill an intermediate section of a thin sample such as to enable an upper portion of the thin sample to tilt in relation to a lower portion of the thin sample; wherein the lower portion is connected to a wafer from which the thin sample was formed; and
    an inspection unit, adapted to direct a charged particle beam towards the upper portion and to collect particles resulting from the illumination.

18. The system according to claim 17 wherein the inspection unit is adapted to collect charged particles reflected or scattered from the thin sample.

19. The system according to claim 17 wherein the inspection unit is adapted to collect particles resulting from an interaction between an inspection aiding material and charged particles that pass through the upper portion of the thin sample.

20. The system according to claim 17 wherein the inspection unit is adapted to collect backscattered electrons resulting from an interaction between an inspection aiding material and charged particles that pass through the upper portion of the thin sample.

21. The system according to claim 17 wherein the inspection unit is adapted to collect x-ray photons resulting from an interaction between an inspection aiding material and charged particles that pass through the upper portion of the thin sample.

22. The system according to claim 17 further comprising an inspection aiding material placement unit, adapted to place an inspection aiding material at a location that is selected such that when the thin sample is illuminated by a charged particle beam multiple charged particles that pass through the tilted upper portion of the thin sample will interact with the inspection aiding material.

23. The system according to claim 22 wherein the inspection aiding material placement unit is adapted to place the inspection aiding material in proximate to the lower portion and below the tilted upper portion.

24. The system according to claim 22 wherein the inspection aiding material placement unit is adapted to place an inspection aiding material that emits backscattered electrons in response to an interaction with the multiple charged particles.

25. The method according to claim 22 wherein the inspection aiding material placement unit is adapted to place an inspection aiding material that emits photons in response to an interaction with the multiple charged particles.

26. The method according to claim 22 comprising placing an inspection aiding material that is adapted to emit x-ray photons in response to an interaction with the multiple charged particles.

27. A system for generating a thin sample, the system comprises:
a miller, adapted to mill an intermediate section of a thin sample such as to enable an upper portion of the thin sample to tilt in relation to a lower portion of the thin sample; wherein the lower portion is connected to a wafer from which the thin sample was formed; and
an inspection aiding material placement unit, adapted to place an inspection aiding material at a location that is selected such that when the thin sample is illuminated by a charged particle beam multiple charged particles that pass through the tilted upper portion of the thin sample will interact with the inspection aiding material.

28. The system according to claim 27 wherein the inspection aiding material placement unit is adapted to place the inspection aiding material in proximate to the lower portion and below the tilted upper portion.

29. The system according to claim 27 wherein the inspection aiding material placement unit is adapted to place an inspection aiding material that emits backscattered electrons in response to an interaction with the multiple charged particles.

30. The method according to claim 27 wherein the inspection aiding material placement unit is adapted to place an inspection aiding material that emits photons in response to an interaction with the multiple charged particles.

31. The system according to claim 27 wherein the inspection aiding material placement unit is adapted to place an inspection aiding material that emits x-ray photons in response to an interaction with the multiple charged particles.

* * * * *